(12) United States Patent
Fasasi et al.

(10) Patent No.: US 11,929,153 B2
(45) Date of Patent: *Mar. 12, 2024

(54) CHEMOMETRIC CHARACTERIZATION OF REFINERY HYDROCARBON STREAMS

(71) Applicant: PHILLIPS 66 COMPANY, Houston, TX (US)

(72) Inventors: Ayuba Fasasi, Bartlesville, OK (US); Alec C. Durrell, Bartlesville, OK (US); Jinfeng Lai, Bartlesville, OK (US); David A. Henning, Bartlesville, OK (US); Franklin Uba, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/065,140

(22) Filed: Dec. 13, 2022

(65) Prior Publication Data

US 2023/0115815 A1 Apr. 13, 2023

Related U.S. Application Data

(63) Continuation-in-part of application No. 17/443,648, filed on Jul. 27, 2021, now Pat. No. 11,557,376.

(51) Int. Cl.
| | |
|---|---|
| *G16B 40/00* | (2019.01) |
| *C10G 75/00* | (2006.01) |
| *G01N 21/3577* | (2014.01) |
| *G01N 21/359* | (2014.01) |
| *G01N 24/08* | (2006.01) |
| *G01N 33/28* | (2006.01) |

(52) U.S. Cl.
CPC ............ *G16B 40/00* (2019.02); *C10G 75/00* (2013.01); *G01N 21/3577* (2013.01); *G01N 21/359* (2013.01); *G01N 24/081* (2013.01); *G01N 24/085* (2013.01); *G01N 33/2823* (2013.01); *C10G 2300/4075* (2013.01)

(58) Field of Classification Search
None
See application file for complete search history.

(56) References Cited

U.S. PATENT DOCUMENTS

| | | | | |
|---|---|---|---|---|
| 2021/0270795 A1* | 9/2021 | Rady | ............. | F17D 3/05 |
| 2023/0113986 A1* | 4/2023 | Fasasi | ............. | G06N 3/126 |
| | | | | 208/14 |
| 2023/0115815 A1* | 4/2023 | Fasasi | ............. | C10G 75/00 |
| | | | | 208/177 |

\* cited by examiner

*Primary Examiner* — Tam M Nguyen
(74) *Attorney, Agent, or Firm* — Phillips 66 Company

(57) ABSTRACT

A process for converting a first hydrocarbon feed stream to one or more liquid transportation fuels in a petroleum refinery where the feed stream is analyzed by at least one analytical method to produce data that is transformed to wavelet coefficients data. A pattern recognition algorithm is trained to recognize subtle features in the wavelet coefficients data that are associated with an attribute of the feed stream. The trained pattern recognition algorithm then rapidly classifies potential hydrocarbon feed streams as a member of either a first group or a second group where the second group comprises hydrocarbon feed streams where the attribute or chemical characteristic at or above a predetermined threshold value. This classification allows rapid decisions to be made regarding utilization of the feedstock in the refinery that may include altering at least one variable in the operation of the refinery.

19 Claims, 10 Drawing Sheets

A.

B.

A.

B.

CHEMOMETRIC CHARACTERIZATION OF REFINERY HYDROCARBON STREAMS

CROSS-REFERENCE TO RELATED APPLICATIONS

This application is a continuation in part application which claims the benefit of and priority to U.S. Provisional Application Ser. No. 63/056,987 filed Jul. 27, 2020, entitled "Rapid Assessment of Crude Oil Fouling Propensity to Prevent Refinery Fouling" and U.S. Utility application Ser. No. 17/443,648 filed Jul. 27, 2021, and entitled "Rapid Assessment of Crude Oil Fouling Propensity to Prevent Refinery Fouling" both of which are hereby incorporated by reference in their entirety.

STATEMENT REGARDING FEDERALLY SPONSORED RESEARCH OR DEVELOPMENT

None.

FIELD OF THE INVENTION

The present invention relates to converting a first hydrocarbon stream to one or more liquid transportation fuels in a petroleum refinery where the hydrocarbon stream is analyzed to produce data that is transformed to wavelet coefficients data and classified by a genetic algorithm into one of two or more groups based upon a particular attribute of the feed stream that is reflected in the wavelets coefficients data. This classification improves conversion efficiency of the hydrocarbon stream to one or more transportation fuels in the refinery.

BACKGROUND

In a commercial refinery, the ability to rapidly assess information regarding the various attributes of a given hydrocarbon stream, (such as, but not limited to, physical or chemical properties, chemical composition, etc.) of hydrocarbon streams is critical to optimizing refinery operations. Refinery operators have long sought rapid processes to rapidly measure certain attributes of refinery hydrocarbon streams in order to maximize fuel production, minimize waste and decrease required maintenance.

Current conventional procedures for predict certain properties of refinery hydrocarbon streams require experimental assays that may take days, or even weeks to complete, which is generally unacceptable in a commercial scale refinery. What is needed are methods that can rapidly predict hydrocarbon stream attributes and can be implemented at reasonable cost.

BRIEF SUMMARY OF THE DISCLOSURE

Some inventive embodiments comprise a process for producing a liquid transportation fuel in a commercial petroleum refinery, comprising: a) analyzing a sample of a first hydrocarbon stream selected from a member of the group consisting of crude petroleum, a crude petroleum fraction, a refinery intermediate stream and a refinery hydrocarbon product by an analytical method selected from mid-infrared spectrometry, near infrared spectrometry, Ramen spectroscopy and nuclear magnetic resonance spectroscopy to produce spectral data comprising a set of discrete digitized data points; b) transforming a subset of the spectral data to produce sample wavelet coefficients data according to wavelet theory by applying a mother wavelet that is a selected from a group consisting of Symlet, Haar and the Coiflets families of mother wavelets, wherein each discrete digitized data point within the subset of the spectral data is converted to a wavelet coefficients data point; c) training a genetic algorithm to classify the sample wavelet coefficients data into one of two groups consisting of a first group and a second group to produce a trained genetic algorithm, where the first group comprises multiple training hydrocarbon streams of distinct origin, wherein each training hydrocarbon stream is selected from the same member of the group as the first hydrocarbon stream of a), where each member of the training hydrocarbon stream has at least one attribute in common that is distinct from the second group, where the training comprises performing the analyzing of part a) on each of the multiple training hydrocarbon streams from both the first group and the second group to produce training wavelets coefficients data and presenting the training wavelets coefficients data obtained from each training hydrocarbon stream to an untrained genetic algorithm that recognizes subtle collective differences within the training wavelet coefficients data obtained from each member of the first group compared to the training wavelet coefficients data obtained from each member of the second group to produce a trained genetic algorithm that successfully associates the collective differences with the presence of the at least one attribute at or above a predetermined threshold level, where the training further comprises an iterative process where each iteration places increasing emphasis on wavelet coefficient data points that increase the probability of accurately classifying the sample into either the first group or the second group; d) classifying the sample of a) as a member of either the first group or the second group by presenting the sample wavelets coefficients data of b) to the trained genetic algorithm, wherein the trained genetic algorithm performs the classifying by examining one or more identifying spectral features that collectively identify the sample as a member of the first group or the second group; e) performing an action selected from: converting the first hydrocarbon feed stream to one or more liquid transportation fuels in a commercial petroleum refinery when the sample of a) is classified as a member of the first group, diluting the first hydrocarbon feed stream with a second hydrocarbon feed stream when the sample of a) is classified as a member of the second group, where the second hydrocarbon feed stream is mixed with the first hydrocarbon feed stream in an amount sufficient to produce a diluted hydrocarbon feed stream comprising less than a threshold quantity of the at least one attribute, then converting the diluted hydrocarbon feed stream to one or more liquid transportation fuels in a commercial petroleum refinery, or not converting the first hydrocarbon feed stream in a commercial petroleum refinery when the sample of a) is classified as a member of the second group.

In some embodiments, the sample spectral data is auto-scaled to produce auto-scaled spectral data by normalizing differences in spectral data signal magnitude.

In some embodiments, the auto-scaled spectral data are vector normalized.

In some embodiments, only a subset of the spectral data is converted to wavelets coefficients data and the genetic algorithm is trained using only the subset, where the subset of spectral data comprises one or more ranges of spectral data having the largest probability of containing spectral features that can be recognized and used by the genetic algorithm to categorize multiple samples into two or more groups.

Some embodiments additionally comprise training the genetic algorithm by curating the set of discrete digitized data points that are initially identified by the untrained genetic algorithm as potentially distinguishing between the first group and the second group to produce a subset of training wavelets coefficients data representing potential identifying data features and presenting the subset of training wavelets coefficients data to the trained genetic algorithm to perform the training of c).

In some embodiments, the analytical method is selected from the group additionally consisting of acoustic spectroscopy, UV-visible spectroscopy, terahertz spectroscopy, mass spectrometry, x-ray spectroscopy, electron energy loss spectroscopy, fluorescence spectroscopy, microwave resonance spectroscopy, surface plasmon resonance spectroscopy and combinations thereof. In some embodiments, the refinery intermediate product is selected from an atmospheric gas oil, a light vacuum gas oil, and a heavy vacuum gas oil. In some embodiments, wherein the at least one attribute is selected from the group consisting of corrosivity, acidity, fouling propensity, sulfur content, boiling point yields at a specific temperature, prevalence of one or more specific chemical functional groups and octane number.

In some embodiments, the wavelet coefficients data is subjected to at least three rounds of decomposition by the mother wavelet. In some embodiments, the mother wavelet is selected from the Symlet family, and the wavelet coefficients data is subjected to at least three rounds of decomposition by the mother wavelet.

Some embodiments comprise a process for producing one or more liquid transportation fuels in a commercial petroleum refinery, comprising: a) analyzing a sample of a hydrocarbon stream selected from a member of the group consisting of crude petroleum, a crude petroleum fraction, a refinery intermediate stream and a refinery hydrocarbon product by an analytical method selected from mid-infrared spectrometry, near infrared spectrometry, Ramen spectroscopy and nuclear magnetic resonance spectroscopy to produce spectral data comprising a set of discrete digitized data points; b) transforming a subset of the spectral data to produce sample wavelet coefficients data according to wavelet theory by applying a mother wavelet that is a selected from a group consisting of Symlet, Haar and the Coiflets families of mother wavelets, where each discrete digitized data point within the subset of the spectral data is converted to a wavelet coefficients data point; c) training a genetic algorithm to classify the sample wavelet coefficients data into one of two groups consisting of a first group and a second group to produce a trained genetic algorithm, where the first group comprises multiple training hydrocarbon streams of distinct origin, where each training hydrocarbon stream is selected from the same member of the group as the first hydrocarbon stream of a), where each member of the training hydrocarbon stream has at least one attribute in common that is distinct from the second group, where the training comprises performing the analyzing of part a) on each of the multiple training hydrocarbon streams from both the first group and the second group to produce training wavelets coefficients data and presenting the training wavelets coefficients data obtained from each training hydrocarbon stream to an untrained genetic algorithm that recognizes subtle collective differences within the training wavelet coefficients data obtained from each member of the first group compared to the training wavelet coefficients data obtained from each member of the second group to produce a trained genetic algorithm that successfully associates the collective differences with the presence of the at least one attribute at or above a predetermined threshold level, where the training further comprises an iterative process where each iteration places increasing emphasis on wavelet coefficient data points that increase the probability of accurately classifying the sample into either the first group or the second group; d) classifying the sample of a) as a member of either the first group or the second group by presenting the sample wavelets coefficients data of b) to the trained genetic algorithm, where the trained genetic algorithm performs the classifying by examining one or more identifying spectral features that collectively identify the sample as a member of the first group or the second group; e) performing an action selected from: converting the hydrocarbon stream in the petroleum refinery to one or more liquid transportation fuels when the sample of a) is classified as a member of the first group, altering at least one variable in operation of the petroleum refinery that increases the yield of one or more liquid transportation fuels when the sample of a) is classified as a member of the second group, and converting the hydrocarbon stream to one or more liquid transportation fuels in the petroleum refinery, rejecting the hydrocarbon stream for conversion to one or more liquid transportation fuels in the petroleum refinery when the sample of a) is classified as a member of the second group.

In some embodiments, the at least one variable in operation of the petroleum refinery is selected from a feed stream feed rate, a distillation temperature, distillation column pump-around rate, process unit temperature, process unit pressure, liquid hourly space velocity for a feed stream or process intermediate product, catalyst choice, catalyst bed temperature, hydrotreating hydrogen consumption rate, and dilution of a feed stream or process intermediate product.

In some embodiments, the sample spectral data is auto-scaled to produce auto-scaled spectral data by normalizing differences in spectral data signal magnitude. In some embodiments, the auto-scaled spectral data are vector normalized. In some embodiments, only a subset of the spectral data is converted to wavelets coefficients data and the genetic algorithm is trained using only the subset, wherein the subset of spectral data comprises one or more ranges of spectral data having the largest probability of containing spectral features that can be recognized and used by the genetic algorithm to categorize multiple samples into two or more groups.

Some embodiments additionally comprise training the genetic algorithm by curating the set of discrete digitized data points that are initially identified by the untrained genetic algorithm as potentially distinguishing between the first group and the second group to produce a subset of training wavelets coefficients data representing potential identifying data features and presenting the subset of training wavelets coefficients data to the trained genetic algorithm to perform the training of c).

In some embodiments, the analytical method is selected from the group additionally consisting of acoustic spectroscopy, UV-visible spectroscopy, terahertz spectroscopy, mass spectrometry, x-ray spectroscopy, electron energy loss spectroscopy, fluorescence spectroscopy, microwave resonance spectroscopy, surface plasmon resonance spectroscopy and combinations thereof.

In some embodiments, the refinery intermediate product is selected from an atmospheric gas oil, a light vacuum gas oil, and a heavy vacuum gas oil. In some embodiments, the at least one attribute is selected from the group consisting of corrosivity, acidity, fouling propensity, sulfur content, boiling point yields at a specific temperature, prevalence of one or more specific chemical functional groups and octane number.

BRIEF DESCRIPTION OF THE DRAWINGS

A more complete understanding of the present invention and its benefits may be acquired by referring to the description provided herein and the accompanying drawings, where.

Figure 1:
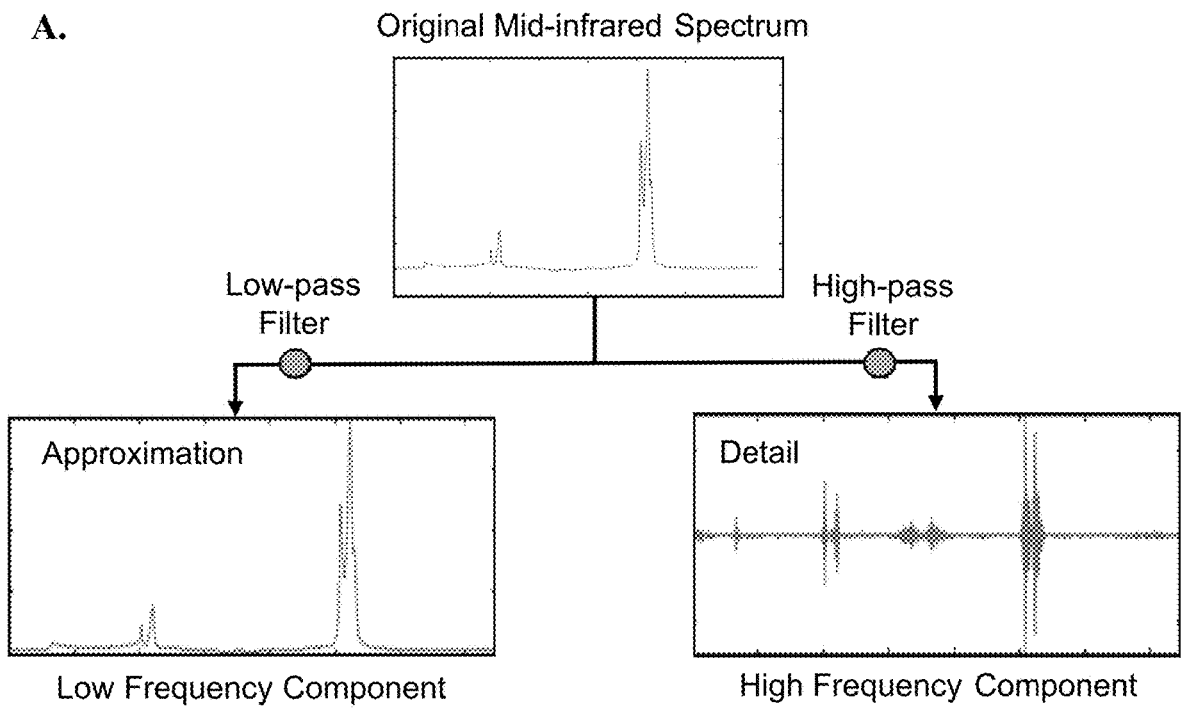
FIG. 1 depicts a diagram demonstrating the decomposition of digitized mid-infrared (MIR) spectral data according to wavelet theory.
Figure 1:
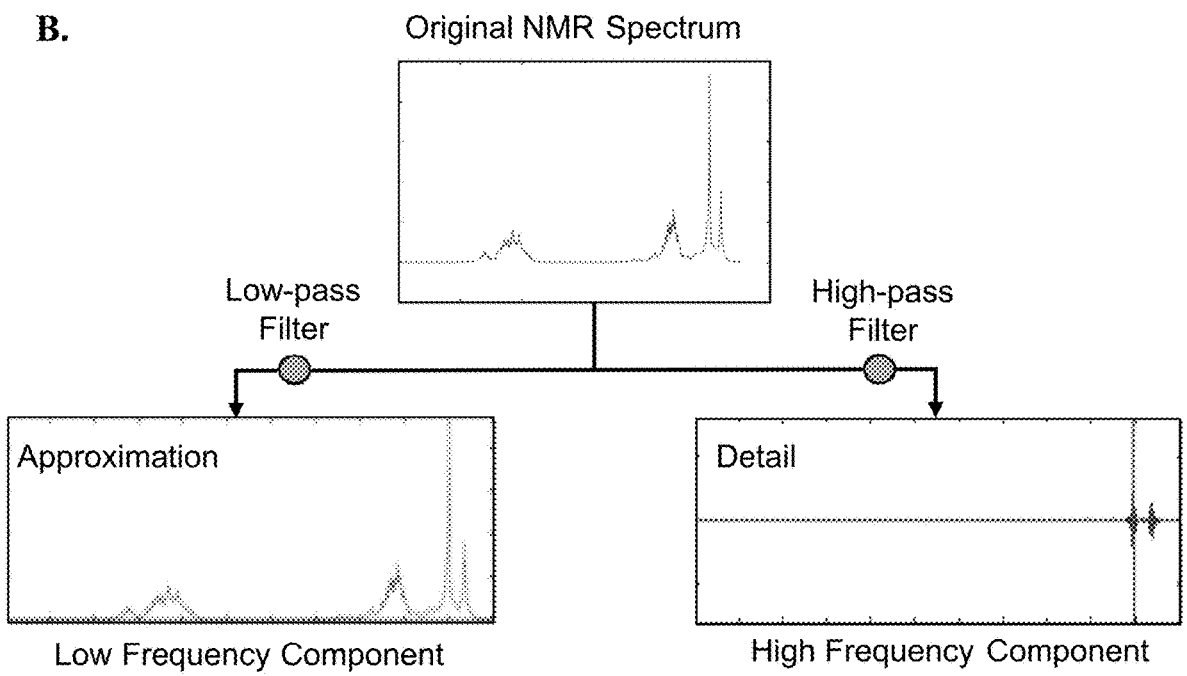

The invention is susceptible to various modifications and alternative forms, specific embodiments thereof are shown by way of example in the drawings. The drawings may not be to scale. It should be understood that the drawings are not intended to limit the scope of the invention to the particular embodiment illustrated.

DETAILED DESCRIPTION

Currently utilized models for predicting any of a number of attributes of the various hydrocarbon streams encountered in a commercial petroleum refinery requires analytical methods to be performed on a sample of these streams that often take hours (or even days) to complete. We sought to develop analytical assays that could rapidly identify one or more distinguishing attributes of a hydrocarbon stream. In some embodiments, the process is utilized to rapidly predict the fouling propensity of a hydrocarbon stream such as a crude petroleum feed stream. Currently utilized models for predicting the fouling propensity of a given sample of crude oil requires crude assay information that can only be obtained by analytical assays that take six hours or more to complete. This greatly hampers the rapid identification of crude oil samples that are capable of fouling process equipment in a commercial refinery setting, leading to potentially increased operating costs.

In other embodiments, the process is utilized to predict corrosivity of a hydrocarbon stream. High-temperature corrosion in petroleum refineries affects piping and equipment operating above 400° F. when hydrocarbons containing naphthenic acid and/or sulfur-containing compounds are present. The ability to predict the corrosivity of crude oils and crude fractions is critical to maintaining safe operation of commercial refineries via prediction of maintenance intervals and also for informing feed stream purchasing decisions.

Some conventional methods for measuring corrosivity of a hydrocarbon stream utilize the total acid number (TAN) and sulfur content, but this approach excludes the potential impact of other chemical compounds as well contributions of individual sulfur and naphthenic acid species. The amount of analytical work required to develop and apply a model that integrates the full level of chemical detail is both cost-prohibitive and too slow to inform feed stream purchasing decisions.

It is well-known that the infrared and nuclear magnetic resonance (NMR) spectral fingerprints of a hydrocarbon is a combination of analytical signals from all species present in the hydrocarbon matrix. Rather than attempting to identify and quantify each individual species from the spectrum, the process disclosed herein shows that a portion of these spectral data may be utilized to create a chemometric model that can rapidly predict the relative corrosion propensity of a given hydrocarbon feed stream (or a refinery intermediate product, such as a gas oil).

The present disclosure comprises a process to measure at least one attribute of a hydrocarbon stream by developing a chemometric model that is based upon digitized spectral data obtained from at least one analytical method, including but not limited to, near-infrared (NIR) spectroscopy, nuclear magnetic resonance (NMR) spectroscopy, mid-infrared (MIR) spectroscopy, Raman spectroscopy acoustic spectroscopy, UV-visible spectroscopy, terahertz spectroscopy, mass spectrometry, x-ray spectroscopy, electron energy loss spectroscopy, fluorescence spectroscopy, microwave resonance spectroscopy, surface plasmon resonance spectroscopy and combinations thereof. The inventive processes and systems disclosed herein successfully distinguish a specific attribute of a hydrocarbon stream (including, but not limited to fouling propensity, corrosivity, sulfur content, acidity, octane rating, chemical composition, etc.) based solely upon analysis of specific features recognized in this spectral data by a genetic algorithm using a specific training process. This represents a significant advance in rapidly characterizing hydrocarbon streams utilized in a commercial petroleum refinery setting.

The inventive process utilizes spectroscopic data that is capable of being used to capture "chemical fingerprints" of hydrocarbon streams that can be correlated with the specific attributes or chemical composition of each sample. For example, MIR spectroscopy provides excited vibrational data while NMR spectroscopy provides data on magnetic field induced molecular chemical shifts that are indicative of the overall molecular composition of each crude oil sample. When utilized together in one embodiment, these two types of data help to more easily identify informative spectral differences between fouling and non-fouling crude oil samples. However, although this distinguishing information is buried within the spectral data, to date it has been impossible to identify these differences solely via attempts to interpret the untransformed spectral data. Although MIR and NMR have the unique advantages of capturing significant identifying information about a crude oil sample (when compared to data obtained by other analytical assays), the complexity and subtlety of these spectral signals has been an obstacle.

The inventive process in part comprises mathematical transformation of the spectral data to wavelet coefficients to enhance subtle but informative features in the data. According to wavelet theory, a discrete signal such as a spectral data point can be decomposed into "approximation" and "detail" components. Wavelet packet transform (WPT) was applied to de-noise and de-convolute digitized spectral data of hydrocarbon samples by decomposing each spectrum into coefficients (wavelet coefficients) that represent the spectrum's constituent frequencies.

Wavelet coefficients offer a different approach to removal of noise from multivariate data than other techniques such as Savitzky-Golay filtering or the fast Fourier transform. Wavelets can often enhance subtle but significant spectral features to increase the general discrimination power of the modeling approach. Using wavelets, a new set of basis vectors is developed in a new pattern space that takes advantage of the local characteristics of the data. These new basis vectors are capable of better conveying the information present in the data than axes that are defined by the original measurement variables.

In the present inventive process, spectral signals were "decomposed" by passing each spectrum through low-pass and high-pass scaling filters to produce a low-frequency "detail" coefficient dataset and a high-frequency "approximation" coefficient dataset. The approximation coefficients correspond to the "low-frequency signal" data in the spectra, while the detail coefficients usually correspond to the "noisy signal" portion of the data. The process of decomposition was continued with different scales of the wavelet filter pair in a step-by-step fashion to separate the noisy components from the signal until the necessary level of signal decomposition was achieved. We have found that wavelet coefficients are especially important and preferred (versus raw spectral data) in modeling corrosion propensity because the nature of the basis vectors used to characterize the data are conducive to a variety of approaches for improving the quality of the input data for training. We found that decomposition of the data using mother wavelets from the Symlet, Haar and Coiflets wavelet families facilitated the recognition of distinct spectral features in the resulting wavelet coefficients data by an untrained genetic algorithm. Through this recognition, the genetic algorithm learned to classify gas oil samples into two groups based upon to the extent that they possessed the specific property being assayed.

As mentioned, the process comprises first obtaining spectral information for a given hydrocarbon stream sample. In some embodiments $^1$H NMR spectral data is obtained. The presence of numerous resonance signals in the $^1$H NMR spectrum is beneficial because those spectral features provide the basis for discrimination between gas oil samples with a high corrosion propensity versus those with low corrosion propensity.

Some embodiments may comprise acquiring $^{13}$C NMR data rather than $^1$H NMR data. While the specifics may differ with regards to chemical shifts, the general concept is identical to the utilization of $^1$H NMR data in conjunction with the present inventive processes. One having average skill in the area of NMR spectroscopy would be familiar with the implementation of $^{13}$C NMR in place of $^1$H NMR data.

Some embodiments comprise obtaining mid-infrared spectral data for a hydrocarbon sample. Mid-infrared spectral data is typically obtained for wavelengths in the range from 400 $cm^{-1}$ to 4000 $cm^{-1}$. Each MIR spectrum is represented by a finite number of discrete digitized data points that typically varies from 50-50,000, alternatively, from 100 to 15,000 discrete digitized data points. In some embodiments, the spectrum may be represented by a quantity of discrete digitized data points that is selected from the range consisting of 300-30,000 discrete digitized data points.

In some embodiments, each MIR spectrum was vector normalized to unit length. This normalized potential minor differences in optical pathlength that may exist between different spectrometers. In some embodiments, the digitized spectral data from each MIR spectrum was auto-scaled to produced auto-scaled spectral data, where the auto-scaling removed inadvertent over-weighting of certain data that would otherwise occur due to differences in signal magnitude across various features of interest. To further enhance informative spectral features, some embodiments included performing a first derivative of each spectrum utilizing a 15-point window, coupled with Savitzky-Golay filtering to assist with model development and testing.

The process utilizes wavelet packet transform to de-noise and de-convolute the spectral data obtained from samples by decomposing each of the discrete digitized data points into coefficients (wavelet coefficients) that represent the constituent frequencies of spectral data obtained from each sample. In some embodiments, only a subset of the digitized spectral data is converted to wavelets coefficients data and the genetic algorithm is trained using only the subset, wherein the subset of spectral data comprises one or more ranges of spectral data having the largest probability of containing spectral features that can be recognized and used by the genetic algorithm to categorize multiple samples into two or more groups. In some embodiments utilizing MIR spectral data, the subset comprises a set of discrete digitized data points in the wavelength ranges from 1300 $cm^{-1}$ to 1800 $cm^{-1}$ and from 2800 $cm^{-1}$ to 3100 $cm^{-1}$. In some embodiments utilizing MIR spectral data, the subset of the spectral data comprises a set of discrete digitized data points in the wavelength range from 1500 $cm^{-1}$ to 1800 $cm^{-1}$.

Wavelets can often enhance subtle but significant spectral features to increase the general discrimination power of the modeling approach. Wavelets offer a different approach to removing noise from multivariate data than Savitzky-Golay filtering or the fast Fourier transform. Using wavelets, a new set of basis vectors are developed that take advantage of the local characteristics of the data, and these vectors convey the information present in the data better than axes defined by the original measurement variables (wavelength). Wavelet coefficients provide the coordinates of the samples in this new pattern space. The mother wavelet selected to develop the new basis set to be the one that best matches the attributes of the data. This prevents accidental correlations between noise (i.e., an interfering source of variation in the data) from obscuring true signal data that correlates with information about the class membership of the samples (e.g., corrosive or non-corrosive, fouling from non-fouling, high octane versus low octane, etc.).

Using wavelet transforms, digitized spectral data points are decomposed by passing each spectral data point through two scaling filters: a high-pass filter and a low-pass filter FIG. 1. The low-pass filter allows only the low-frequency component of the signal to be measured as a set of wavelet coefficients, which is called the "approximation." The high-pass filter measures the high-frequency coefficient set, which is called the "detail." The detail coefficients usually correspond to the noisy part of the data. FIG. 1A shows an example of how this filter separation looks using Mid-Infrared (MIR) spectral data, while FIG. 1B shows an example of how this filter separation looks using Nuclear magnetic resonance (NMR) spectral data.

Figure 2:
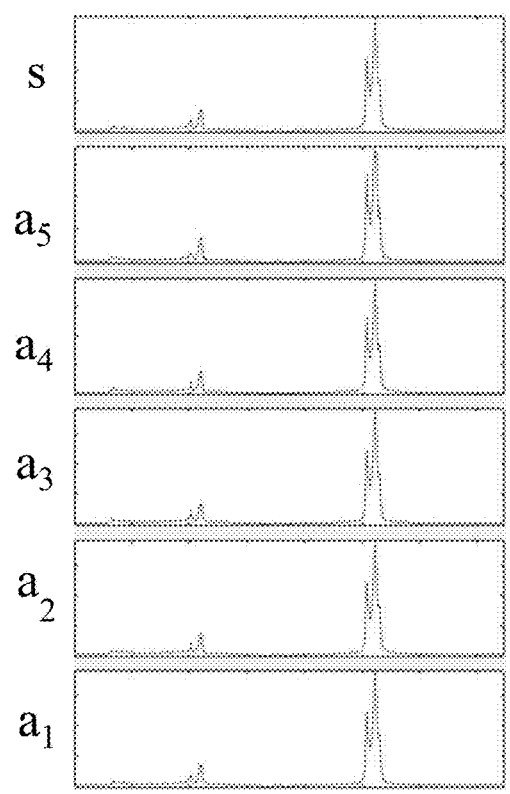
FIG. 2 depicts progressive decomposition of MIR spectral data to produce approximation (a) and detail (d) coefficients data from the first to sixth levels.
Figure 2:
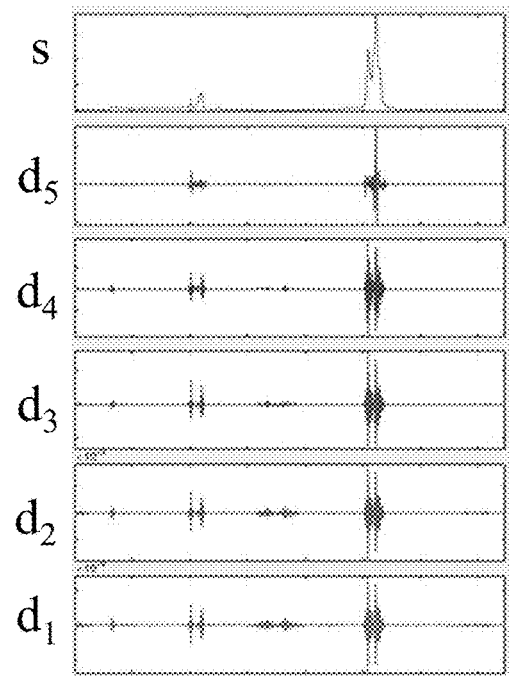
Figure 2:
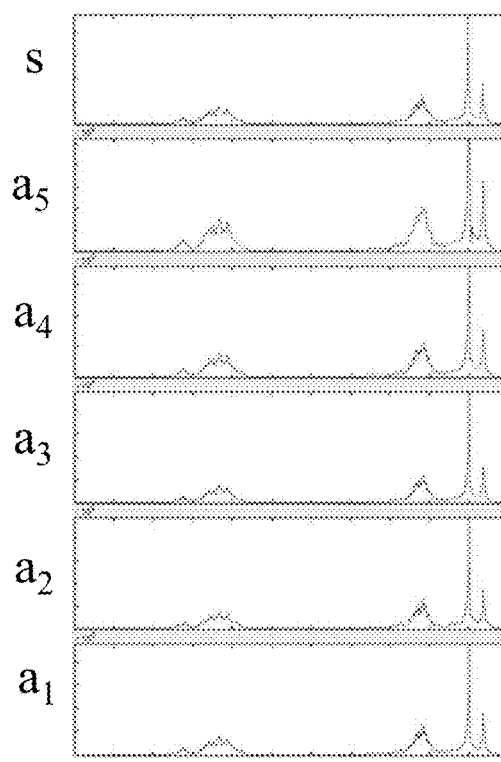
Figure 2:
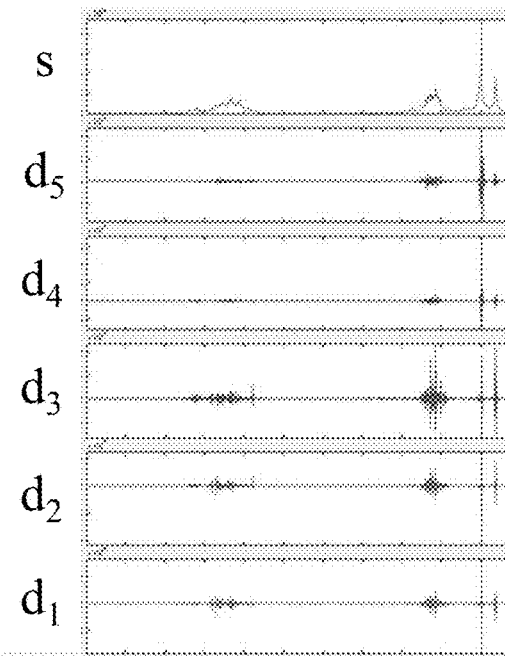

This process of decomposition is continued with different scales of the wavelet filter pair in a step-by-step fashion to separate the noisy components from the signal until the necessary level of decomposition has been achieved. FIG. 2A displays the results of wavelet decomposition of MIR spectral data performed up to the sixth level for the approximation ($a_1$-$a_6$) and detail ($d_1$-$d_6$) components, where "s" indicates the original MIR spectrum. FIG. 2B displays the results of wavelet decomposition of NMR spectral data performed up to the sixth level for the approximation ($a_1$-$a_6$) and detail ($d_1$-$d_6$) components, where "s" indicates the original NMR spectrum. A decrease in "noise" is visually evident beyond the third level of decomposition of the spectral data following being passed through a high pass filter.

Wavelet coefficients are especially important and are preferred to raw spectral data for modeling many physical properties and compositional attributes of hydrocarbon streams because the nature of the basis vectors used to characterize the data is conducive to a variety of approaches for improving the quality of the data that is used for model training. The wavelet coefficients obtained from the digitized data points for each spectrum are organized as a data vector. In some embodiments each coefficient is auto-scaled to remove inadvertent weighing of the data that would otherwise occur due to differences in magnitude across measurement variables.

A mother wavelet is selected to develop the new basis set, and historically, certain classes of mother wavelet have been commonly utilized that are considered to be the most effective at extracting distinguishing class information from spectral data. Selecting a mother wavelet to use as a "reference point" helps solve the problem that occurs when an interfering source of variation in the data is correlated to information about the class membership of the samples as a result of the design of the study or because of accidental correlations between signal and noise.

Some embodiments of the present inventive process utilize a mother wavelet from one of the Symlet, Haar or Coiflets families of mother wavelets. For these embodiments, the process may apply a mother wavelet at the third or greater level of decomposition; alternatively, the fourth level of decomposition or greater; alternatively, the fifth level of decomposition. The choice of the mother wavelet at the third level of decomposition or greater was found to enhance the rather subtle but informative spectral features in the data. This resulted in an improved ability of the inventive process to discriminate between hydrocarbon streams with a significant difference in a at least one physical property and/or compositional attribute and to classify hydrocarbon streams into two or more different groups separated by a predetermined threshold value for that property or constituent.

Some embodiments of the process generally comprise training a genetic algorithm or utilizing support vector machines to distinguish between wavelet coefficients data for samples comprising gas oil that are highly corrosive to refinery process equipment versus those that are not. A genetic algorithm is a search heuristic that is inspired by Charles Darwin's theory of natural evolution. This algorithm reflects the process of natural selection where the fittest individuals are selected for reproduction in order to produce offspring of the next generation. The process of natural selection starts with the selection of fittest individuals (i.e., data points) from a population. They produce offspring which inherit the characteristics of the parents and will be added to the next generation. If parents have better fitness, their offspring will be better than parents and have a better chance at surviving. This process is iterative and eventually results in a generation with the fittest individuals identified. The specifics of training and applying genetic algorithms to data is familiar to those having experience in the field of data analysis, and thus a more detailed explanation is not provided here.

In some embodiments of the present inventive process, a genetic algorithm for pattern-recognition analysis is trained to identify distinguishing features within wavelet coefficients data derived from digitized spectral data obtained from analyzing a gas oil, thereby producing a trained genetic algorithm that can classify gas oil samples into two groups depending on their relative capacity to corrode refinery equipment (or not). In some embodiments of the present inventive process, a genetic algorithm for pattern-recognition analysis is trained to identify distinguishing features within wavelet coefficients data derived from digitized spectral data obtained from analyzing a crude petroleum, thereby producing a trained genetic algorithm that can classify crude petroleum samples into two groups depending on their relative propensity to foul refinery equipment.

In some embodiments, the process additionally employs one or more data pre-processing methods in order to improve identification of data point outliers caused by either 1) "masking" (i.e., poor quality data points that are masked by other poor quality data points) or 2) "swamping" (i.e., bad data points that make good data points look like poor quality data). Some embodiments implement auto-scaling of the digitized spectral data prior to conversion to wavelet coefficients. This removes inadvertent over-weighting of some data that would otherwise occur due to differences in the signal magnitude of features found within certain wavelength regions of the digitized spectral data. Some embodiments utilize baseline correction of the digitized spectral data in the spectral regions utilized for training a pattern recognition genetic algorithm. To further enhance informative spectral features, some embodiments comprise calculating a first derivative of the digitized data points for each spectrum utilizing a 15-point window, coupled with Savitzky-Golay filtering for model development and testing.

In certain embodiments, the genetic algorithm is trained using spectral data obtained from five or more distinct aliquots of gas oil or crude oil having different characteristics, with each aliquot preferably of distinct geologic origin. Certainly, a larger number of distinct aliquots is preferred and will result in a trained genetic algorithm that can better discriminate between corrosive and non-corrosive samples. In certain embodiments, training the genetic algorithm to distinguish between corrosive and non-corrosive samples may utilize the spectral data obtained from at least 20, at least 35, or at least 50 distinct aliquots obtained from a variety of different geologic sources.

The pattern-recognition genetic algorithm may utilize both supervised learning and unsupervised learning to identify the wavelet coefficients data that corresponds to vibrational spectroscopic features (from MIR data) and/or chemical shifts (from NMR data) that facilitate the ability of the genetic algorithm to classify each hydrocarbon sample as either corrosive or non-corrosive. In embodiments that comprise supervised learning, manual curation to exclude certain data features is performed based upon the probability that such features may have resulted from areas of the spectral data with a low signal to noise ratio. The result of such manual curation is a subset of features (often the two or three largest principal components of the data as recognized by the genetic algorithm) that is utilized by the trained genetic algorithm to classify each sample comprising crude oil. Pattern-recognition by the genetic algorithm of spectral feature differences representing the principal components in the sample maximizes the variance between groups (i.e., corrosive versus non-corrosive samples), which also maximizes the percentage of data utilized by the pattern recognition genetic algorithm to classify each sample that is derived from spectral differences between the groups. A principal-component plot that shows separation of the samples into two groups can be generated using only a curated subset of spectral features that provide the most information about the differences between the samples, simplifying classification based upon a given characteristic or property (e.g., corrosive propensity). This fitness criterion (i.e., the curated subset) dramatically reduces the size of the search space because it limits the classification search to a small number of spectral features within the wavelet coefficients data that are capable of distinguishing the corrosive propensity of an unknown (or uncharacterized) sample into one of the two or more classes/clusters.

In addition, as the pattern-recognition genetic algorithm trains, it focuses on those samples that are difficult to classify by boosting the relative importance (or weighting) of distinguishing spectral features associated with those samples. Over time, the genetic algorithm learns in a manner similar to how a neural network learns. The pattern-recognition genetic algorithm integrates aspects of artificial intelligence and evolutionary computations to yield the trained genetic algorithm of the present inventive processes and systems.

The training wavelet coefficients data obtained from aliquots of the first group are collectively compared to the training wavelet coefficients data obtained from aliquots of the second group by the pattern recognition genetic algorithm, wherein the genetic algorithm performs an iterative process that with each iteration gives added weight (or significance) to the wavelet coefficients data that best distinguishes between the two groups. This iterative process eventually distinguishes spectral features that differ between the first group (viewed collectively) and the second group, thereby producing a trained genetic algorithm. The trained genetic algorithm is then capable of quickly classifying a sample as a member of the first or the second group.

Figure 3:
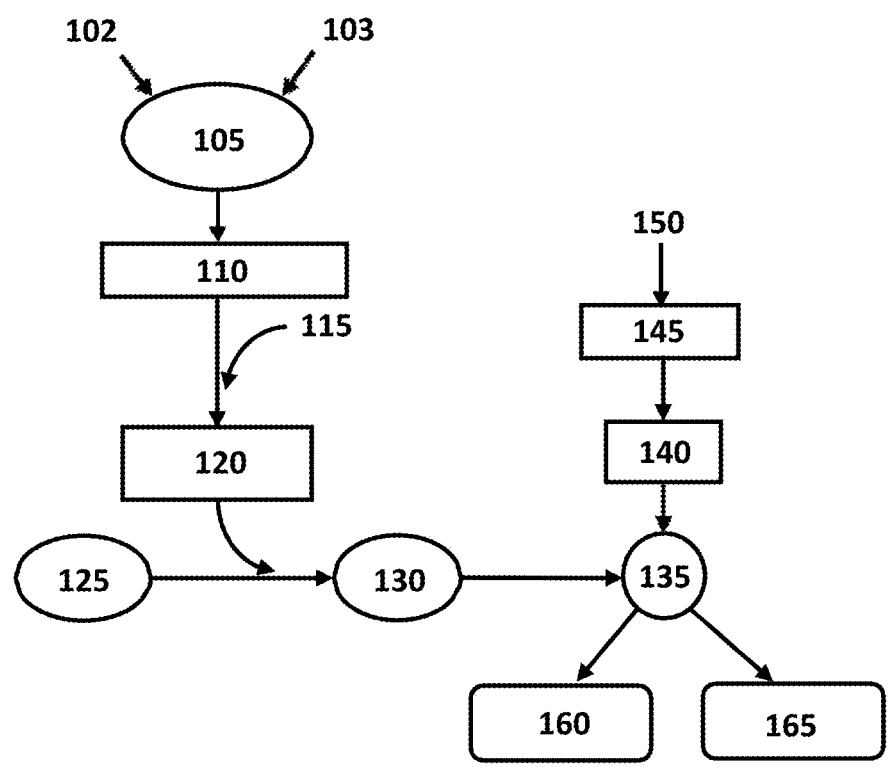
FIG. 3 is a simplified diagram depicting a first embodiment of the present inventive process and system.

A first embodiment of the inventive process and system is illustrated by the flow diagram of FIG. 3. In general terms, the embodiment comprises training a genetic algorithm to recognize subtle collective differences within data obtained from two groups, a first group comprising aliquots of non-fouling crude oil that are each characterized by a fouling thermal resistance of less than 0.002 hr-ft$^2$-° F./BTU and a second group comprising aliquots of crude oil that are each characterized by a fouling thermal resistance of at least 0.002 hr-ft$^2$-° F./BTU and are capable of causing fouling in petroleum refinery processes and equipment.

In the embodiment shown in FIG. 3, multiple aliquots comprising crude petroleum that are collectively referred to as the first group 102 and multiple aliquots comprising crude petroleum that are collectively referred to as the second group 103 are analyzed by a spectral method 105 comprising at least one of NIR spectroscopy and NMR spectroscopy to produce spectral data 110, where the spectral data obtained for each aliquot by spectral method 105 comprises multiple distinct digitized data points. Each of the first group 102 and the second group 103, respectively, comprise at least five aliquots, where each aliquot is preferably of distinct geologic origin from others within the group and in the case of the second group, each aliquot is characterized by a different fouling thermal resistance of at least 0.002 hr-ft$^2$-° F./BTU.

The spectral data 110 for each aliquot is transformed to training wavelet coefficients data 120 according to wavelet theory by processing the data using a mother wavelet 115 that comprises a member of the Symlet family of mother wavelets. In certain embodiments, a member of the Symlet mother wavelet family that is selected from the Symlet4 and Symlet6 mother wavelets. The mother wavelet 115 is utilized to mathematically decompose the spectral data 110 according to wavelet theory to the third level of decomposition or greater to produce training wavelet coefficients data 120. Commercially available computer software (for example, but not limited to, MATLAB®) may be employed to facilitate the iterative decomposition process, but such software is not essential in order to practice the inventive process as described herein.

The embodiment trains a genetic algorithm, which comprises presenting an untrained genetic algorithm 125 that designed to perform data pattern recognition with the training wavelet coefficients data 120 obtained from each of the multiple aliquots comprising the first group 102 and the second group 103, respectively. While training, the untrained genetic algorithm 125 recognizes subtle patterns, or spectral features that are located within the training wavelet coefficients data 120 to produce a trained genetic algorithm 130 that utilizes the potential differentiating data features to classify a given sample comprising crude oil as either non-fouling or fouling.

The trained genetic algorithm 130 is operable to recognize differentiating data features within sample wavelets coefficients data 140 that is derived from the sample spectral data 145 of an uncharacterized sample 150 comprising crude oil. The trained genetic algorithm 130 then classifies the uncharacterized sample 150 comprising crude oil as an either first group feed stream 160 or a second group feed stream 165 wherein the first group feed stream 160 comprises a non-fouling crude oil sample characterized by a fouling thermal resistance of less than 0.002 hr-ft$^2$-° F./BTU and the second group feed stream 165 comprises a fouling crude oil test sample characterized by a fouling thermal resistance of at least 0.002 hr-ft$^2$-° F./BTU.

The uncharacterized sample 150 is analyzed by NIR and/or NMR spectroscopy in a similar (or identical) way as was described for the multiple aliquots comprising the first group 102 and the second group 103 to acquire the sample digitized spectral data 145. The sample digitized spectral data 145 is converted to sample wavelets coefficients data 140 that is then presented to the trained genetic algorithm 135. The trained genetic algorithm 135 recognizes differentiating data features within the sample wavelets coefficients data 140, which enables the trained genetic algorithm 135 to classify the uncharacterized sample 150 as a member of either the first group 160 or the second group 165.

Some embodiments additionally comprise manually curating potential differentiating features in the wavelets coefficients data, wherein potential differentiating features are identified by the pattern recognition genetic algorithm. Manual curation eliminates potential differentiating features with the highest probability of being falsely associated with a given property or characteristic (i.e., derived from a region of the spectral data that is characterized by a low signal to noise ratio).

Figure 4:
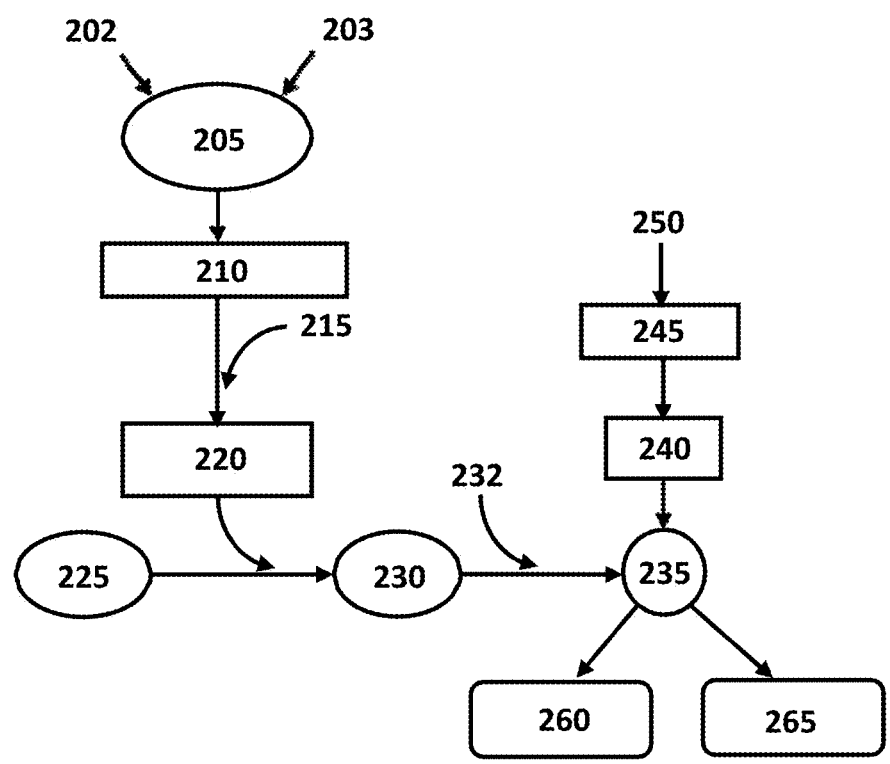
FIG. 4 is a simplified diagram depicting a second embodiment of the present inventive process and system.

An embodiment of the inventive process and system that includes this optional manual curation of the data is illustrated by the flow diagram of FIG. 4. The embodiment comprises training a pattern-recognition genetic algorithm to recognize subtle collective differences within data obtained from two groups, a first group comprising aliquots of a sample comprising a gas oil that are each characterized by a corrosivity of 7 mils per year (mpy) or less and a second group comprising aliquots of a sample comprising gas oil that are each characterized by a corrosivity of greater than 7 mpy and that are typically capable of causing significant corrosion inside reactors, conduits and heat exchangers of a commercial petroleum refinery.

The training wavelet coefficients data obtained from aliquots of the first group feeds are collectively compared to the training wavelet coefficients data obtained from aliquots of the second group feeds by the genetic algorithm, wherein the genetic algorithm performs an iterative process that eventually distinguishes spectral features that differ between the first group feeds (viewed collectively) and the second group feeds, thereby producing a trained genetic algorithm. The trained genetic algorithm is then capable of quickly classifying a sample having an unknown corrosivity as a member of either a first group feed stream or a second group feed stream.

In the embodiment shown in FIG. 4, multiple aliquots of liquid hydrocarbons of a gas oil or crude oil that collectively comprise the first group feed 202 and multiple aliquots of liquid hydrocarbons of a gas oil or crude petroleum that collectively comprise the second group feed 203 are analyzed by a spectroscopy method 205 comprising at least one of MIR and NMR to produce spectral data 210, where the spectral data obtained for each aliquot by spectral method 205 comprises multiple distinct digitized data points. Each of the first group 202 and the second group 203, respectively, comprise at least five aliquots, where each aliquot is preferably of distinct geologic origin (in the case of crude oil) or obtained from a different refinery (in the case of gas oil), and in the case of the second group, each aliquot is characterized by a different corrosion propensity.

The spectral data 210 for each aliquot is transformed to training wavelet coefficients data 220 according to wavelet theory by processing the data using a mother wavelet 215 that comprises a member of the Symlet, Haar or Coiflets family of mother wavelets. The mother wavelet 215 is utilized to decompose the spectral data 210 to the third level of decomposition or greater to produce training wavelet coefficients data 220. Some embodiments may employ commercially available computer software (for example, but not limited to, MATLAB®) to facilitate the iterative decomposition process, but such software is not essential in order to practice the inventive process as described herein.

The embodiment trains a genetic algorithm, which comprises presenting an untrained genetic algorithm 225 that is designed to perform data pattern recognition with the training wavelet coefficients data 220 obtained from each of the multiple aliquots comprising the first group 202 and the second group 203, respectively. While training, the untrained genetic algorithm 225 recognizes subtle patterns, or spectral features that are located within the training wavelet coefficients data 220 to produce a trained genetic algorithm intermediate 230.

Further referring to the embodiment depicted in FIG. 4, potential differentiating data features that are recognized by the untrained genetic algorithm 225 are then subjected to manual curation 232 to produce a trained genetic algorithm 235 that utilizes a curated subset of the potential differentiating data features to classify a given sample comprising crude oil as either non-fouling or fouling. Manual curation 232 of potential differentiating data features comprises eliminating from consideration any potential differentiating data features recognized by the trained genetic algorithm intermediate 230 that are deemed by either a process operator or an automated curation process to have a high probability of contributing to an inaccurate classification. Potential differentiating data features most likely to be subject to manual curation typically are located in a region of the spectral data where the data is typically characterized by a low signal to noise ratio. The trained genetic algorithm 235 is characterized by a curated subset of differentiating data features, which makes the trained genetic algorithm 235 operable to recognize differentiating data features within sample wavelets coefficients data 240 that is derived from the MIR or NMR spectral data 245 of an uncharacterized sample 250. The trained genetic algorithm 235 then classifies the uncharacterized sample 250 as an either first group feed stream 260 or a second group feed stream 265 wherein a first group feed stream 260 comprising a non-corrosive crude oil or gas oil sample characterized by a corrosion rate 7 mpy or less and a second group feed stream 265 comprising a corrosive crude oil or gas oil sample that is characterized by a corrosion rate of greater than 7 mpy.

The uncharacterized sample 250 is analyzed by MIR or NMR in a similar (or identical) way as was described for the multiple aliquots comprising the first group 202 and the second group 203 to acquire the MIR and/or NMR spectral data 245. The MIR and/or NMR spectral data 245 is converted to sample wavelets coefficients data 240 that is then presented to the trained genetic algorithm 235. The trained genetic algorithm 235 recognizes differentiating data features within the sample wavelets coefficients data 240, which enables the trained genetic algorithm 235 to classify the uncharacterized sample 250 as a member of either the first group 260 or the second group 265.

Some embodiments more broadly comprise converting the hydrocarbon stream in the petroleum refinery to one or more liquid transportation fuels when the sample of is classified as a member of the first group. However, when the sample is classified as a member of the second group, the process may instead comprise altering at least one variable in operation of the petroleum refinery that improves the yield of one or more liquid transportation fuels, before converting the hydrocarbon stream to one or more liquid transportation fuels in the petroleum refinery. Alternatively, when the sample of is classified as a member of the second group, the hydrocarbon feed stream may be rejected for conversion to one or more liquid transportation fuels in the petroleum refinery. In some embodiments, the at least one variable in operation of the petroleum refinery that is altered is selected from a feed stream feed rate, a distillation temperature, distillation column pump-around rate, process unit temperature, process unit pressure, liquid hourly space velocity for a feed stream or process intermediate product, catalyst choice, catalyst bed temperature, hydrotreating hydrogen consumption rate, and dilution of a feed stream or process intermediate product. Certainly other variables are well-understood in the field of refining and could additionally be altered or adjusted despite being not categorically listed here.

The following examples of certain embodiments of the invention are given. Each example is intended to illustrate a specific embodiment, but the scope of the invention is not intended to be limited to the embodiments specifically disclosed. Rather, the scope is intended to be as broad as is supported by the complete disclosure and the appending claims.

Example 1

A set of 27 different gas oils were obtained from multiple commercial refinery sources located on different continents and tested for corrosion potential using conventional methods. This set of gas oils were then utilized to train a genetic algorithm to differentiate high corrosivity gas oils from low corrosivity gas oils. Gas oils were sourced from prior distillations of whole crudes, as well as samples derived from crude oils sourced from California, Canada, South America, West Africa, the Middle East, and the North Sea. Gas oils tested included atmospheric gas oils (AGOs), light vacuum gas oils (LVGOs), and heavy vacuum gas oils (HVGOs). The corrosivity of these gas oils was first determined via a conventional autoclave corrosion test, then analyzed by mid-infrared (Mid-IR) and NMR spectroscopy.

A sample of each gas oil (150 g) was added to a Parr Instruments 300-mL autoclave. Four metal coupons (A516gr70 carbon steel, 5-chrome steel, 9-chrome steel, and 410 stainless steel) were rinsed with toluene and acetone, dried, and weighed. The coupons were then inserted into a ceramic holder containing the gas oil and placed in the autoclave. Samples were heated to 550° F. for 24 hr. The mixture was stirred at 200 rpm and a flow of nitrogen gas was passed through the gas oil at a rate of 7 sccm during the test. After the mixture cooled, the metal coupons were removed from the gas oil, rinsed with toluene and acetone and allowed to dry. The coupons were then photographed. Bead blasting was used to remove any scale that formed during the test, after which each coupon was weighed. The difference in weight before and after the test was used to calculate a corrosion rate, measured as mils per year (mpy) of thickness loss. Measured corrosion rates for the gas oils tested ranged from 3 to 24 mpy.

All gas oils were analyzed neat (i.e., without further preparation) on a Nicolet iS50 Mid-IR Spectrometer. Experimental measurements were performed in attenuated total reflectance (ATR) mode using the diamond internal reflection element. Spectra were collected using 32 scans at 4 cm−1 spectral resolution. MIR spectra were measured using a KBr beam splitter and deuterated triglycine sulfate (DTGS) detector with a potassium bromide (KBr) window allowing collection from 4000 $cm^{-1}$ to 400 $cm^{-1}$. No modifications of the ATR accessory were necessary for data acquisition. Thermo-Nicolete OMNIC® software was used to acquire all gas oil spectra and the processed spectra were saved in .spa file format.

Figure 5:
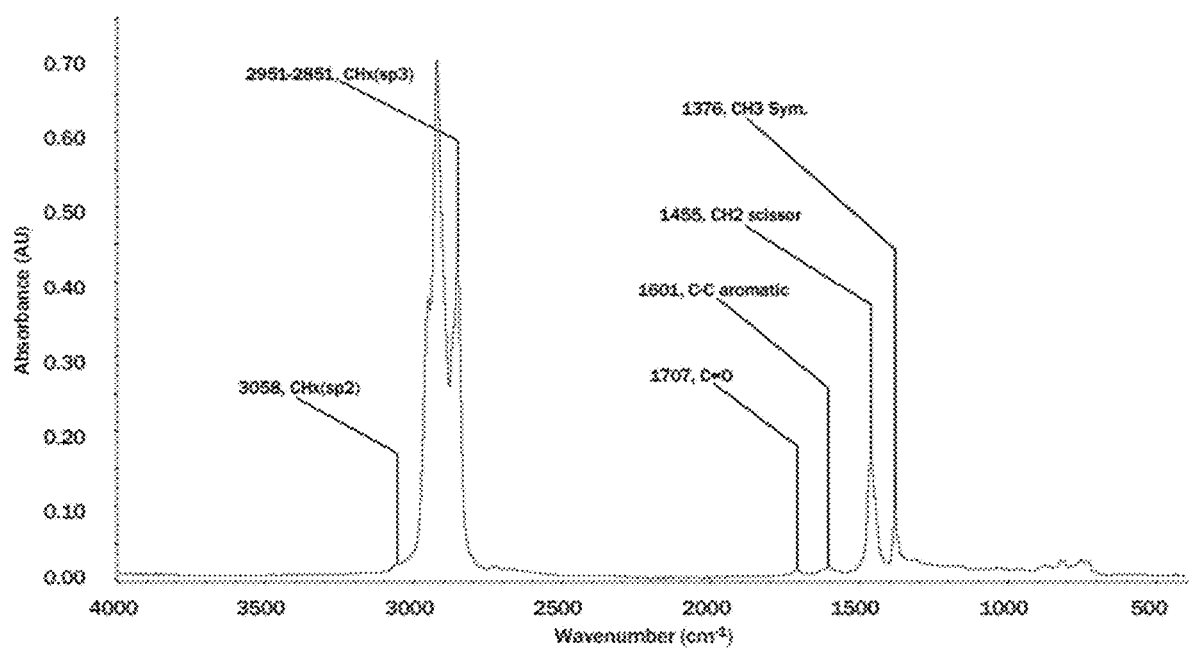
FIG. 5 depicts a typical representative MIR spectrum for one sample comprising gas oil.
Figure 6:
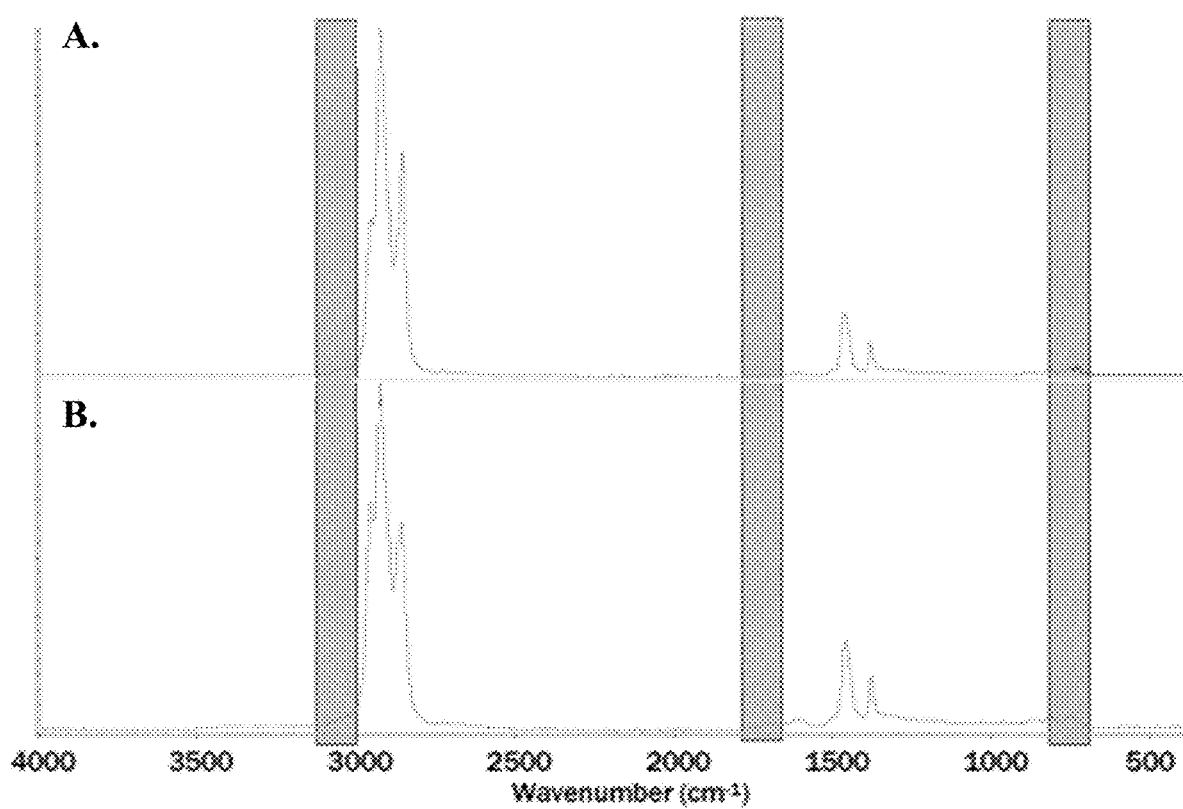
FIG. 6 depicts two stacked MIR spectrums for samples comprising gas oil to demonstrate spectral regions thought to be associated with differences in corrosive propensity.

FIG. 5 shows the MIR spectrum of a typical gas oil sample. Labels on the spectrum show the wavelengths indicative of asymmetric stretching vibrational bands associated with $CH_x(sp_2)$, $CH_x(sp_3)$, carbonyl (C=O), $CH_2$ scissor and $CH_3$ functional groups. These features are associated with the presence and quantity of olefins and/or aromatics, carbonyls, and aliphatic hydrocarbons. To better understand the spectral differences between high and low corrosivity gas oils, a MIR spectrum for a low corrosivity gas oil is shown in FIG. 6A, and a MIR spectrum for a high-corrosivity gas oil is shown in (FIG. 6B), respectively. Comparison of these spectra initially suggested that three spectral regions (outlined by shaded bars) differentiate low corrosivity gas oils from high corrosivity gas oils. High corrosivity gas oils appeared to be relatively rich in aromatics and olefins (seen at the 3050 $cm^{-1}$ and 1600 $cm^{-1}$ shaded regions) while gas oils having lower corrosivity appeared to be enriched in longer aliphatic hydrocarbon chains (see 720 $cm^{-1}$ vibrational bands). As evident in FIG. 6B, the carbonyl (C=O) peak, at 1700 $cm^{-1}$, appeared more prevalent in the high corrosivity gas oils and may have been associated with the presence of naphthenic acids in the oil.

Gas oil samples were also analyzed using NMR spectroscopy. NMR spectra were obtained on a Bruker Avance III HD 400 NMR spectrometer operating at 400.16 MHz for proton ($^1H$) and 100.04 MHz for carbon ($^{13}C$). Chloroform-d was used as a solvent. Samples were run at 25° C. Tetramethylsilane (TMS) was used as an internal chemical-shift reference (0 ppm) for $^1H$. All the chemical shifts are reported in ppm relative to TMS. Sixty-four scans with a 45° pulse were acquired for all $^1H$ NMR experiments.

Figure 7:
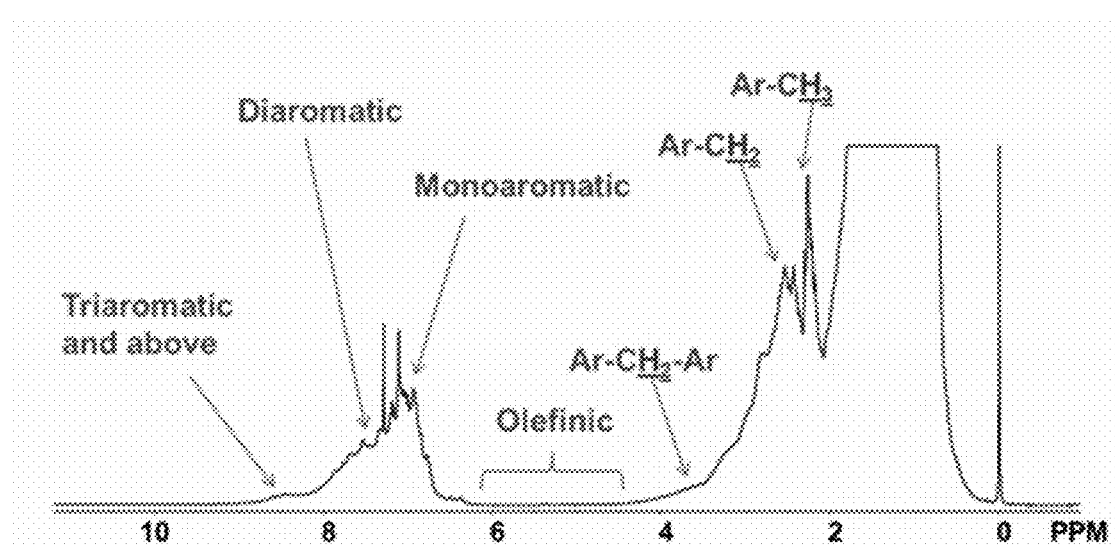
FIG. 7 depicts a typical representative $^1$H NMR spectrum for one sample comprising gas oil.
Figure 8:
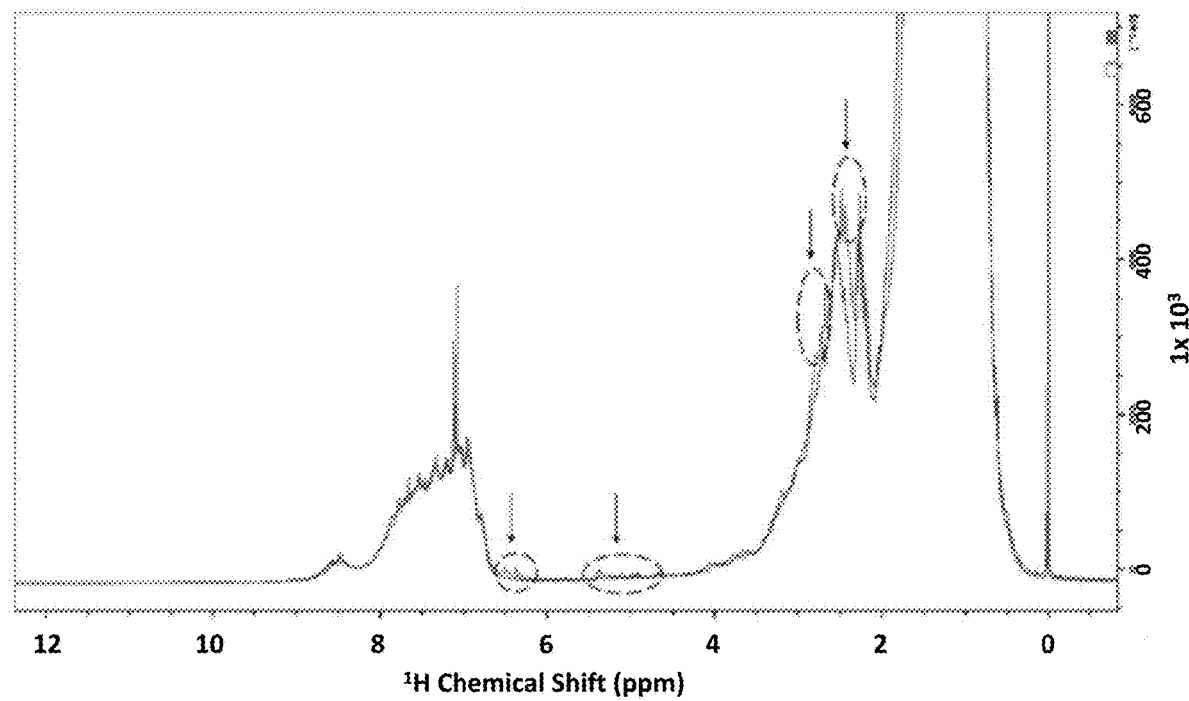
FIG. 8 depicts overlaid $^1$H NMR spectrums for two gas oil samples comprising gas oil.

FIG. 7 shows a typical 1H NMR spectrum for a gas oil sample and indicates the functional groups believed to be associated with some resonance features in the spectrum. FIG. 8 shows an overlay of two $^1H$ NMR spectrums corresponding to both a high corrosivity gas oil (12.7 mpy) and a low corrosivity gas oil (3.3 mpy) sample. Dotted circles highlight regions that appeared to display spectral differences between a high-corrosion and low-corrosion gas oil. These differences were observed in several $^1H$ NMR chemical shift regions and their assignments are:

2.2-2.6 ppm: aliphatics bound to carboxylate or sulfur
2.6-2.9 ppm: aliphatics bound to nitrogen
4.5-6.0 ppm, olefins
6.2-6.6 ppm, aromatics bound to nitrogen The results suggested a possible correlation between corrosivity and the presence of carboxylate, sulfur, nitrogen, and olefin species in gas oils. These spectral sub-regions were further investigated using the process disclosed herein.

Example 2

The digitized spectral data obtained in EXAMPLE 1 by both MIR and NMR was then transformed by wavelet packet transform according to wavelet theory to produce wavelet coefficients data. Each spectrum comprising near-infrared spectral data was decomposed according to wavelet theory using a mother wavelet from the Haar, Symlet or Coiflets family of mother wavelets. Decomposition comprised passing the spectral data through two scaling filters: a high pass filter and a low pass filter. As mentioned previously, FIG. 1 illustrates how the high-pass scaling filter allowed only the high-frequency component of the original spectral data to be converted to a "detail coefficient data set", while the low-pass scaling filter allowed only the low-frequency component of the original spectral data to be converted to an "approximation coefficient data set". Commercially available computer software (for example, but not limited to MATLAB®) may be employed to assist in this transformation but is not required in order to practice the inventive process as described herein.

The process of signal decomposition was continued with different scales of the wavelet filter pair in a step-by-step fashion to separate the noisy components from the signal until the appropriate level of signal decomposition was achieved. Applying the Symlet2 mother wavelet to MIR digitized MIR data, it was determined that the fifth level of decomposition or greater allowed sufficient discrimination of signal from noise to readily distinguish corrosive samples from non-corrosive samples. In certain embodiments, the fourth level of decomposition or greater allowed discrimination of signal from noise.

The decomposed wavelet coefficient data for each sample were used to train a pattern-recognition genetic algorithm to recognize potential spectral features that might allow the algorithm to distinguish between samples characterized as "corrosive" (i.e., greater than 7 mpy) and samples characterized as "non-corrosive" (i.e., corrosiveness of 7 mpy or less). Training a pattern-recognition genetic algorithm comprised presenting an untrained genetic algorithm (designed for pattern recognition) with the training wavelet coefficients data obtained from the multiple aliquots representing the first group and the second group, respectively.

Figure 9:
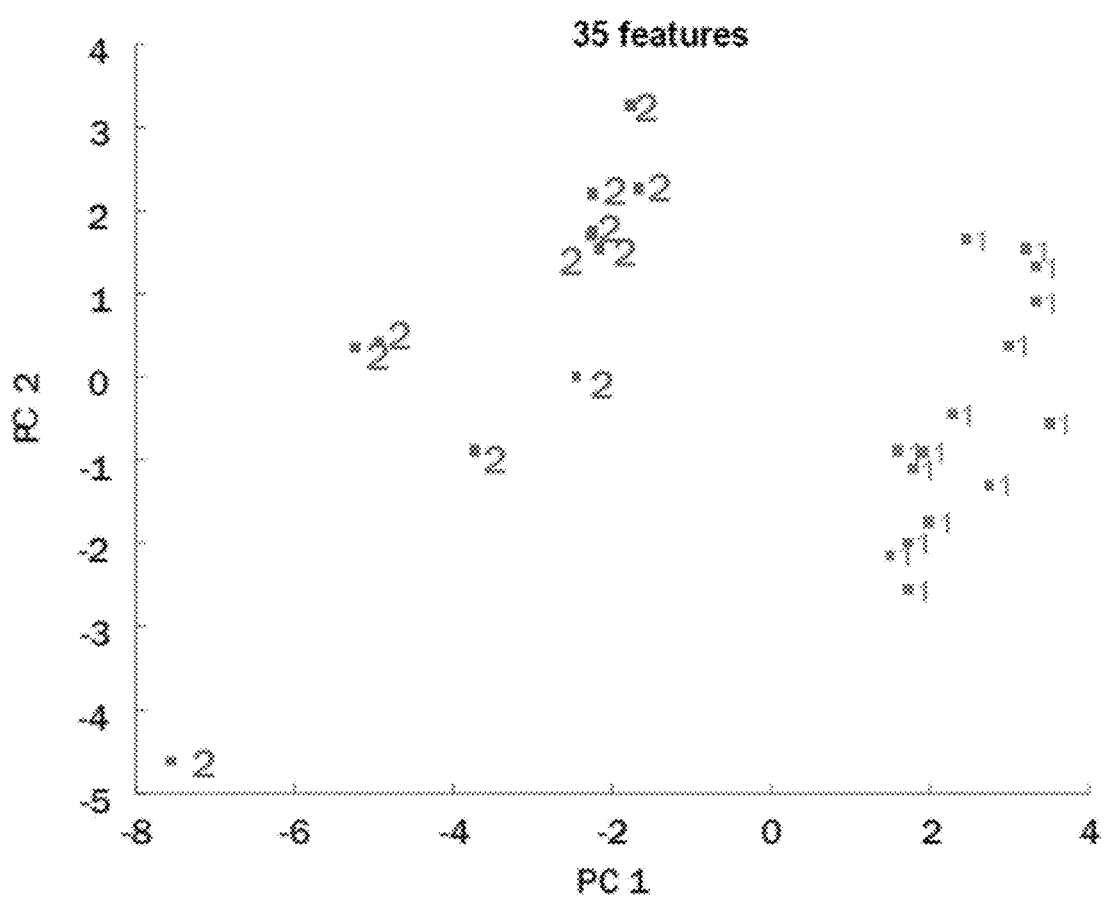
FIG. 9 is a principal components plot where each data point represents a different gas oil sample that has been classified into one of two groups by a trained pattern recognition genetic algorithm.
Figure 10:
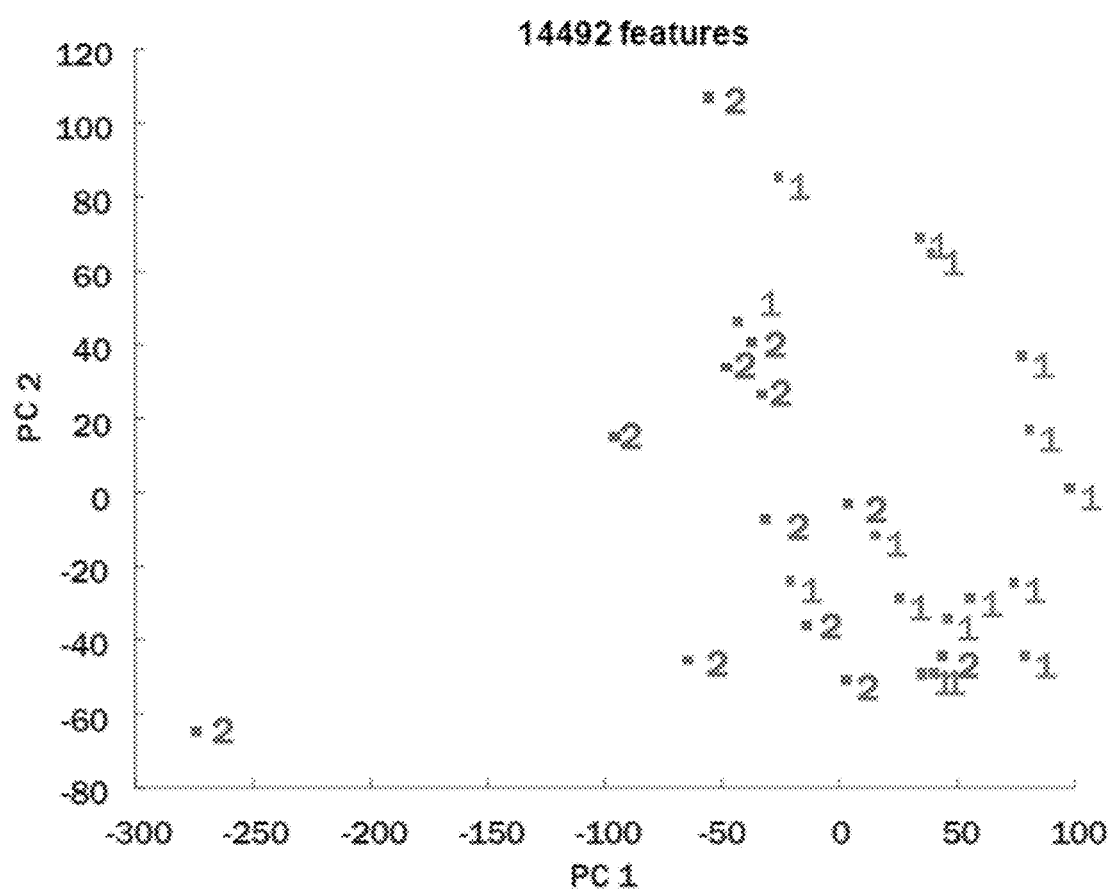
FIG. 10 is a principal components plot where each data point represents a different gas oil sample that has been classified into one of two groups by a trained pattern recognition genetic algorithm.

Decomposition of MIR spectral data using the Symlet2 mother wavelet at the fifth level of decomposition enabled a genetic algorithm to distinguish spectral features in the resulting wavelet coefficients data that enabled classification of gas oil samples into two groups based on their high temperature corrosivity propensity. As the genetic algorithm examined the data and identified potential features in the wavelets coefficients data that could assist in differentiating between the two classes, certain identified potential features were eliminated by manual curation to eliminate identified potential features with the highest probability of being a false positive (i.e., derived from a region of the data that is characterized by a low signal to noise ratio). The process of manual curation can also be thought of as a "search pre-filtering" that pre-screens data that is used by the final trained genetic algorithm to classify samples. Manual curation or pre-filtering served to: 1) decrease the total data to be reviewed by the genetic algorithm when classifying a sample, and 2) assure that potential features that were the result of noise in the data were not utilized by the trained genetic algorithm during classification samples comprising crude oil. The remaining features that were utilized by the trained genetic algorithm for classification typically were associated with spectral features associated with the 2-3 most prevalent classes of chemical compounds in the sample. The model presented in FIG. 9, which demonstrates curation of the data to include only a subset of 35 selected features, shows good separation between high- and low-corrosivity samples, allowing accurate classification. In contrast, the uninformative un-curated model shown in FIG. 10 utilized the entire set of 14492 wavelet coefficients and was unable to clearly distinguish whether a sample belonged to either of the two groups. Referring again to FIG. 9, none of the 35 selected features were located too close in distance to the intersection of the two zero lines of the principal components. This indicates that these features were indeed highly informative regarding differentiating between the two groups and also suggest that none of the 35 selected features is noise. Once the pattern recognition genetic algorithm was trained using the various training aliquots, the trained genetic algorithm was competent to accurately classify the relative corrosion potential of unknown samples comprising gas oil. Even in challenging trials, the present inventive method correctly classified a variety of samples as either corrosive or non-corrosive via the identification of two or more selected discriminating features that were developed from wavelet coefficients data and identified by a pattern-recognition genetic algorithm.

Although the systems and processes described herein have been described in detail, various changes, substitutions, and alterations can be made without departing from the spirit and scope of the invention as delineated by the following claims. Further, the description, abstract and drawings are not intended to limit the scope of the claims to the embodiments disclosed.

In the present description, the term corrosion is intended to have its normal customary meaning, describing the degradation of materials by corrosion. Corrosivity as used herein refers to relative potential of a substance (e.g., a gas oil or crude oil) to cause corrosion in a commercial refinery setting, which leads to increased maintenance costs and decreased refinery production.

In the present description, the term attribute refers to any physical property, chemical property or difference in chemical composition that can be distinguished between two or more hydrocarbons streams.

We claim:

1. A process for producing a liquid transportation fuel in a petroleum refinery, comprising:
   a) analyzing a sample of a first hydrocarbon stream selected from a member of the group consisting of crude petroleum, a crude petroleum fraction, a refinery intermediate stream and a refinery hydrocarbon product by an analytical method selected from mid-infrared spectrometry, near infrared spectrometry, Ramen spectroscopy and nuclear magnetic resonance spectroscopy to produce spectral data comprising a set of discrete digitized data points;
   b) transforming a subset of the spectral data to produce sample wavelet coefficients data according to wavelet theory by applying a mother wavelet that is a selected from a group consisting of Symlet, Haar and the Coiflets families of mother wavelets, wherein each discrete digitized data point within the subset of the spectral data is converted to a wavelet coefficients data point;
   c) training a genetic algorithm to classify the sample wavelet coefficients data into one of two groups consisting of a first group and a second group to produce a trained genetic algorithm,
      wherein the first group comprises multiple training hydrocarbon streams of distinct origin, wherein each training hydrocarbon stream is selected from the same member of the group as the first hydrocarbon stream of a), wherein each member of the training hydrocarbon stream has at least one attribute in common that is distinct from the second group,
      wherein the training comprises performing the analyzing of part a) on each of the multiple training hydrocarbon streams from both the first group and the second group to produce training wavelets coefficients data and presenting the training wavelets coefficients data obtained from each training hydrocarbon stream to an untrained genetic algorithm that recognizes subtle collective differences within the training wavelet coefficients data obtained from each member of the first group compared to the training wavelet coefficients data obtained from each member of the second group to produce a trained genetic algorithm that successfully associates the collective differences with the presence of the at least one attribute at or above a predetermined threshold level, wherein the training further comprises an iterative process wherein each iteration places increasing emphasis on wavelet coefficient data points that increase the probability of accurately classifying the sample into either the first group or the second group;
   d) classifying the sample of a) as a member of either the first group or the second group by presenting the sample wavelets coefficients data of b) to the trained genetic algorithm, wherein the trained genetic algorithm performs the classifying by examining one or more identifying spectral features that collectively identify the sample as a member of the first group or the second group;
   e) performing an action selected from:
      converting the first hydrocarbon feed stream to one or more liquid transportation fuels in a commercial petroleum refinery when the sample of a) is classified as a member of the first group, diluting the first hydrocarbon feed stream with a second hydrocarbon feed stream when the sample of a) is classified as a member of the second group, wherein the second hydrocarbon feed stream is mixed with the first hydrocarbon feed stream in an amount sufficient to produce a diluted hydrocarbon feed stream comprising less than a threshold quantity of the at least one attribute, then converting the diluted hydrocarbon feed stream to one or more liquid transportation fuels in a commercial petroleum refinery, or not converting the first hydrocarbon feed stream in a commercial petroleum refinery when the sample of a) is classified as a member of the second group.

2. The process of claim 1, wherein the sample spectral data is auto-scaled to produce auto-scaled spectral data by normalizing differences in spectral data signal magnitude.

3. The process of claim 2, wherein the auto-scaled spectral data are vector normalized.

4. The process of claim 1, wherein only a subset of the spectral data is converted to wavelets coefficients data and the genetic algorithm is trained using only the subset, wherein the subset of spectral data comprises one or more ranges of spectral data having the largest probability of containing spectral features that can be recognized and used by the genetic algorithm to categorize multiple samples into two or more groups.

5. The process of claim 1, additionally comprising training the genetic algorithm by curating the set of discrete digitized data points that are initially identified by the untrained genetic algorithm as potentially distinguishing between the first group and the second group to produce a subset of training wavelets coefficients data representing potential identifying data features and presenting the subset of training wavelets coefficients data to the trained genetic algorithm to perform the training of c).

6. The process of claim 1, wherein the analytical method is selected from the group additionally consisting of acoustic spectroscopy, UV-visible spectroscopy, terahertz spectroscopy, mass spectrometry, x-ray spectroscopy, electron energy loss spectroscopy, fluorescence spectroscopy, microwave resonance spectroscopy, surface plasmon resonance spectroscopy and combinations thereof.

7. The process of claim 1, wherein the refinery intermediate product is selected from an atmospheric gas oil, a light vacuum gas oil, and a heavy vacuum gas oil.

8. The process of claim 1, wherein the at least one attribute is selected from the group consisting of corrosivity, acidity, fouling propensity, sulfur content, boiling point yields at a specific temperature, prevalence of one or more specific chemical functional groups and octane number.

9. The process of claim 1, wherein the wavelet coefficients data is subjected to at least three rounds of decomposition by the mother wavelet.

10. The process of claim 1, wherein the mother wavelet is selected from the Symlet family, and the wavelet coefficients data is subjected to at least three rounds of decomposition by the mother wavelet.

11. A process for producing one or more liquid transportation fuels in a commercial petroleum refinery, comprising:

a) analyzing a sample of a hydrocarbon stream selected from a member of the group consisting of crude petroleum, a crude petroleum fraction, a refinery intermediate stream and a refinery hydrocarbon product by an analytical method selected from midinfrared spectrometry, near infrared spectrometry, Ramen spectroscopy and nuclear magnetic resonance spectroscopy to produce spectral data comprising a set of discrete digitized data points;

b) transforming a subset of the spectral data to produce sample wavelet coefficients data according to wavelet theory by applying a mother wavelet that is a selected from a group consisting of Symlet, Haar and the Coiflets families of mother wavelets, wherein each discrete digitized data point within the subset of the spectral data is converted to a wavelet coefficients data point;

c) training a genetic algorithm to classify the sample wavelet coefficients data into one of two groups consisting of a first group and a second group to produce a trained genetic algorithm, wherein the first group comprises multiple training hydrocarbon streams of distinct origin, wherein each training hydrocarbon stream is selected from the same member of the group as the first hydrocarbon stream of a), wherein each member of the training hydrocarbon stream has at least one attribute in common that is distinct from the second group, wherein the training comprises performing the analyzing of part a) on each of the multiple training hydrocarbon streams from both the first group and the second group to produce training wavelets coefficients data and presenting the training wavelets coefficients data obtained from each training hydrocarbon stream to an untrained genetic algorithm that recognizes subtle collective differences within the training wavelet coefficients data obtained from each member of the first group compared to the training wavelet coefficients data obtained from each member of the second group to produce a trained genetic algorithm that successfully associates the collective differences with the presence of the at least one attribute at or above a predetermined threshold level, wherein the training further comprises an iterative process wherein each iteration places increasing emphasis on wavelet coefficient data points that increase the probability of accurately classifying the sample into either the first group or the second group;

d) classifying the sample of a) as a member of either the first group or the second group by presenting the sample wavelets coefficients data of b) to the trained genetic algorithm, wherein the trained genetic algorithm performs the classifying by examining one or more identifying spectral features that collectively identify the sample as a member of the first group or the second group;

e) performing an action selected from:

converting the hydrocarbon stream in the petroleum refinery to one or more liquid transportation fuels when the sample of a) is classified as a member of the first group, altering at least one variable in operation of the petroleum refinery that increases the yield of one or more liquid transportation fuels when the sample of a) is classified as a member of the second group, and converting the hydrocarbon stream to one or more liquid transportation fuels in the petroleum refinery, rejecting the hydrocarbon stream for conversion to one or more liquid transportation fuels in the petroleum refinery when the sample of a) is classified as a member of the second group.

12. The process of claim 11, wherein the at least one variable in operation of the petroleum refinery is selected from a feed stream feed rate, a distillation temperature, distillation column pump-around rate, process unit temperature, process unit pressure, liquid hourly space velocity for a feed stream or process intermediate product, catalyst choice, catalyst bed temperature, hydrotreating hydrogen consumption rate, and dilution of a feed stream or process intermediate product.

13. The process of claim 11, wherein the sample spectral data is auto-scaled to produce auto-scaled spectral data by normalizing differences in spectral data signal magnitude.

14. The process of claim 13, wherein the auto-scaled spectral data are vector normalized.

15. The process of claim 11, wherein only a subset of the spectral data is converted to wavelets coefficients data and the genetic algorithm is trained using only the subset, wherein the subset of spectral data comprises one or more ranges of spectral data having the largest probability of containing spectral features that can be recognized and used by the genetic algorithm to categorize multiple samples into two or more groups.

16. The process of claim 11, additionally comprising training the genetic algorithm by curating the set of discrete digitized data points that are initially identified by the untrained genetic algorithm as potentially distinguishing between the first group and the second group to produce a subset of training wavelets coefficients data representing potential identifying data features and presenting the subset of training wavelets coefficients data to the trained genetic algorithm to perform the training of c).

17. The process of claim 11, wherein the analytical method is selected from the group additionally consisting of acoustic spectroscopy, UV-visible spectroscopy, terahertz spectroscopy, mass spectrometry, x-ray spectroscopy, electron energy loss spectroscopy, fluorescence spectroscopy, microwave resonance spectroscopy, surface plasmon resonance spectroscopy and combinations thereof.

18. The process of claim 11, wherein the refinery intermediate product is selected from an atmospheric gas oil, a light vacuum gas oil, and a heavy vacuum gas oil.

19. The process of claim 11, wherein the at least one attribute is selected from the group consisting of corrosivity, acidity, fouling propensity, sulfur content, boiling point yields at a specific temperature, prevalence of one or more specific chemical functional groups and octane number.

* * * * *